US007270966B2

(12) United States Patent
Communi et al.

(10) Patent No.: US 7,270,966 B2
(45) Date of Patent: *Sep. 18, 2007

(54) HUMAN PYRIMIDINE RECEPTOR

(75) Inventors: Didier Communi, Braine le Chateau (BE); Marc Parmentier, Beersel (BE); Jean-Marie Boeynaems, Wemmel (BE); Sabine Pirotton, Brussels (BE)

(73) Assignee: Euroscreen SA (BE)

( * ) Notice: Subject to any disclaimer, the term of this patent is extended or adjusted under 35 U.S.C. 154(b) by 221 days.

This patent is subject to a terminal disclaimer.

(21) Appl. No.: 10/753,695

(22) Filed: Jan. 8, 2004

(65) Prior Publication Data

US 2004/0175766 A1 Sep. 9, 2004

Related U.S. Application Data

(62) Division of application No. 09/077,173, filed on Nov. 12, 1998, now Pat. No. 6,790,626.

(30) Foreign Application Priority Data

Nov. 21, 1995 (EP) .................................. 95870124

(51) Int. Cl.
*G01N 33/53* (2006.01)
*C12Q 1/68* (2006.01)
(52) U.S. Cl. ........................................... 435/7.2; 435/6
(58) Field of Classification Search ..................... None
See application file for complete search history.

(56) References Cited

U.S. PATENT DOCUMENTS 6,790,626 B2 * 9/2004 Communi et al. ........... 435/7.2

FOREIGN PATENT DOCUMENTS

| WO | WO95/10538 | 4/1995 |
| WO | WO96/38558 | 12/1996 |

OTHER PUBLICATIONS

Barnard, et al., "G protein-coupled receptors for ATP and other nucelotides: a new receptor family", TIPS 15:67-70 (1994).
Boarder, et al., "G protein-coupled P₂ purinoceptors: from molecular biology to functional responses", TIPS 16:133-139 (1995).
Boyer, et al., "Differential effects of P₂-purinoceptor antagonists on phospholipase C- and adenylyl cyclase-coupled P$_{2Y}$-purinoceptors", Br. J. Pharmacol. 113:614-620 (1994).
Brake, et al., "New Structural motif for ligan-gated ion channels defined by an ionotropic ATP receptor", Nature 371:519-523 (1994).
Brown, et al., "Evidence that UTP and ATP Regulate Phospholipase C through a Common Extracellular 5'-Nucleotide Receptor in Human Airway Epithelial Cells", Molecular Pharmacology 40:648-655 (1991).
Communi, et al., "Cloning and Functional Expression of a Human Uridine Nucleotide Receptor", J. Biol. Chem. 270(52):30849-30852 (1995).
Communi, et al., "Coexpression of P$_{2Y}$ and P$_{2U}$ Receptors on Aortic Endothelial Cells", Circulation Research 76(2):191-198 (1995).
Devereus, et al., "A comprehensive set of sequence analysis programs for the VAX", Nucleic Acids Research 12(1):387-395 (1984).
Erb, et al., "Functional expression and photoaffinity labeling of a cloned P$_{2U}$ purinergic receptor", Proc. Natl. Acad. Sci. USA 90:10449-10453 (1993).
Erb, et al., "Site-directed Mutagenesis of P$_{2U}$ Purinoceptors", J. Biol. Chem. 270(9):4185-4188 (1995).
Filz, et al., "Expression of a Cloned P$_{2Y}$ Purinergic Receptor that Couples to Phospholipase C", Molecular Pharmacology 46:8-14 (1994).
Fredholm, et al., "VI. Nomenclature and Classification of Purinoceptors", Pharmacological Reviews 46(2):143-156.
Harrison, et al., "cDNA cloning of a G-protein-coupled receptor expressed in rat spinal cord and brain related to chemokine receptors", Neuroscience Letters 169:85-89 (1994).
Henderson, et al., "Cloning and Characterization of a Bovine P$_{2Y}$ Receptor", Biochem. Biophys. Research Comm. 212(2):648-656 (1995).
Kaplan, et al., "Identification of a G Protein Couple Receptor Induced in Activated T Cells", J. Immun. 151(2):628-636 (1993).
Lazarowski, et al., "Identification of a Uridine Nucleotide-selective G-protein-linked Receptor That Activates Phospholipase C", J. Biol. Chem. 269(16):11830-11836 (1994).
Libert, et al., "Selective Amplification and Cloning of Four New Members of the G Protein-Coupled Receptor Family", Science 244:569-572 (1989).
Lustig, et al., "Expression cloning of an ATP receptor from mouse neuroblastoma cells", Proc. Natl. Acad. Sci. USa 90:5113-5117 (1993).
Motte, et al., "Evidence that most High-affinity ATP binding sites on aortic endothelial cells and membrances do not respond to P₂ receptors", Eur. J. Pharm. 307:201-209 (1996).
Nomura, et al., "Molecular cloning of cDNAs encoding a LD 78 receptor and putative leukocyte chemotactic peptide receptors", International Immun. 5(10):1239-1249 (1993).

(Continued)

*Primary Examiner*—Ruixiang Li
(74) *Attorney, Agent, or Firm*—Edwards Angell Palmer & Dodge; Kathleen Williams; Amy DeCloux

(57) ABSTRACT

This invention provides a receptor having a preference for pyrimidine nucleotides preferably uridine triphosphate over purine nucleotides. A receptor having a preference for pyrimidine nucleotides over purine nucleotides means a receptor for which pyrimidine nucleotides and purine nucleotides are not equally active and equipotent. This means that the receptor according to the invention in presence of these agonists presents a functional response (preferably the accumulation of Inositol triphosphate (IP3), diacylglycerol (DAG), or calcium ions) to lower concentration of pyrimidine nucleotides, preferably uridine triphosphate, than to purine nucleotides or a more important functional response to similar concentration of pyrimidine nucleotide than to purine nucleotide

2 Claims, 12 Drawing Sheets

OTHER PUBLICATIONS

O'Conner, et al., "Further subclassification of ATP receptors based on agonist studies", TIPS 12:137-141 (1991).

Parr, et al., "Cloning and expression of a human $P_{2U}$ nucleotide receptor, a target for cystic fibrosis pharmacotherapy", Proc. Natl. Acad. Sci. USA 91:3275-3279 (1994).

Rice, et al., "Cloning and Expression of the Alvolar Type II Cell $P_{2U}$-Purinergic Receptor", Am. J. Respir. Cell Mol. Biol. 12:27-32 (1995).

Seifert, et al., "Involvement of pyrimidinoceptors in the regulation of cell functions by uridine and by uracil nucleotides", TiPS 10:365-369 (1989).

Stam, et al., "Molecular cloning and characterization of a novel orphan receptor ($P_{2P}$) expressed in human pancreas that shows high structural homology to the $P_{2U}$ purinoceptor", FEBS Letters 384:260-264 (1996).

Tokuyama, et al., "Cloning of Rat and mouse $P_{2Y}$ Purinoceptors", Biochem. and Biophys. Research Comm. 211(1):211-218 (1995).

Valera, et al., "A new class of ligand-gated ion channel defined by $P_{2X}$receptor for extracellular ATP", Nature 371:516-519 (1994).

Velu, et al., "Retroviruses Expressing Different Levels of the Normal Epidermal Growth Factor Receptor: Biological Properties and New Bioassay", J. Cell. Biochem. 39:153-166 (1989).

Webb, et al., "Cloning and functional expression of a brain G-protein-coupled ATP receptor", FEBS Letters 324(2):219-225 (1993).

Zeng, et al., "Molecular characterization of a rat $\alpha_{2D}$-adrenergic receptor", Proc. Natl. Acad. Sci. USA 87:3102-3106 (1990).

\* cited by examiner

```
       AAGGGAGCTTGGGTAGGGGCCAGGCTAGCCTGAGTGCACCCAGATGCGCTTCTGTCAGCT     60
       CTCCCTAGTGCTTCAACCACTGCTCTCCCTGCTCTACTTTTTTTGCTCCAGCTCAGGGAT    120
       GGGGGTGGGCAGGGAAATCCTGCCACCCTCACTTCTCCCCTTCCCATCTCCAGGGGGCC     180

1   ATGGCCAGTACAGAGTCCTCCCTGTTGAGATCCCTAGGCCTCAGCCCAGGTCCTGGCAGC    240
   1    M  A  S  T  E  S  S  L  L  R  S  L  G  L  S  P  G  P  G  S

61   AGTGAGGTGGAGCTGGACTGTTGGTTTGATGAGGATTTCAAGTTCATCCTGCTGCCTGTG    300
  21    S  E  V  E  L  D  C  W  F  D  E  D  F  K  F  I  L  L  P  V

121   AGCTATGCAGTTGTCTTTGTGCTGGGCTTGGGCCTTAACGCCCCAACCCTATGGCTTTTC    360
  41    S  Y  A  V  V  F  V  L  G  L  G  L  N  A  P  T  L  W  L  F

181   ATCTTCCGCCTCCGACCCTGGGATGCAACGGCCACCTACATGTTCCACCTGGCATTGTCA    420
  61    I  F  R  L  R  P  W  D  A  T  A  T  Y  M  F  H  L  A  L  S

241   GACACCTTGTATGTGCTGTCGCTGCCCACCCTCATCTACTATTATGCAGCCACAACCAC     480
  81    D  T  L  Y  V  L  S  L  P  T  L  I  Y  Y  Y  A  A  H  N  H

301   TGGCCCTTTGGCACTGAGATCTGCAAGTTCGTCCGCTTCTTTCTATTGGAACCTCTAC     540
 101    W  P  F  G  T  E  I  C  K  F  V  R  F  F  L  L  E  P  L  Y

361   TGCAGTGTCCTTTTCCTCACCTGCATCAGCGTGCACCGCTACCTGGGCATCTGCCACCCA    600
 121    C  S  V  L  F  L  T  C  I  S  V  H  R  Y  L  G  I  C  H  P

421   CTTCGAGCACTACGCTGGGGCCGCCCTCGCCTCGCAGGCCTTCTCTGCTGGCAGTTGG     660
 141    L  R  A  L  R  W  G  R  P  R  L  A  G  L  L  C  L  A  V  W

481   TTGGTCGTAGCCGGCTGCCTCGTGCCCAACCTGTTCTTTGTCACAACCAGCAACAAAGGG    720
 161    L  V  V  A  G  C  L  V  P  N  L  F  F  V  T  T  S  N  K  G

541   ACCACCGTCCTGTGCCATGACACCACTCGGCCTGAAGAGTTTGACCACTATGTGCACTTC    780
 181    T  T  V  L  C  H  D  T  T  R  P  E  E  F  D  H  Y  V  H  F

601   AGCTCAGCGGTGATGGGCCTGCTCTTTGGCGTGCCTGCCTGGTCACTCTTGTTTTGTAT    840
 201    S  S  A  V  M  G  L  L  F  G  V  P  A  L  V  T  L  V  C  Y

661   GGACTCATGGCTCGTCGCCTGTATCAGCCCTTGCCAGGCTCTGCACAGTCGTCTTTTCGC    900
 221    G  L  M  A  R  R  L  Y  Q  P  L  P  G  S  A  Q  S  S  R

721   CTCCGCTCTCTCCGCACCATAGCTGTGGTGCTGACTGTCTTTGCTGTCTGCTTTCGTGCT    960
 241    L  R  S  L  R  T  I  A  V  V  L  T  V  F  A  V  C  F  V  P

781   TTCCACATCACCCGCACCATTTTACTACCTGGCCAGGCTGTTGGAAGCTGACTGCCGAGTA   1020
 261    F  H  I  T  R  T  I  L  L  P  G  Q  A  V  G  S  *  L  P  S

841   CTGAACATTGTCAACGTGGTCTATAAAGTGACTCGGCCCCTGGCCAGTGCCAACAGCTGC   1080
 281    L  N  I  V  N  V  V  Y  K  V  T  R  P  L  A  S  A  N  S  C

901   CTGGATCCTGTGCTCTACTTGCTCACTGGGGACAAATATCGACGTCAGCTCCGTCAGCTC   1140
 301    L  D  P  V  L  Y  L  L  T  G  D  K  Y  R  R  Q  L  R  Q  L

961   TGTGGTGGTGGCAAGCCCCAGCCCCGCACGGCTGCCTCTTCCCTGGCACTAGTGTCCCTG   1200
 321    C  G  G  G  K  P  Q  P  R  T  A  A  S  S  L  A  L  V  S  L

1021   CCTGAGGATAGCAGCTGCAGGTGGGCGGCCACCCCCAGGACAGTAGCTGCTCTACTCCT   1260
 341    P  E  D  S  S  C  R  W  A  A  T  P  Q  D  S  S  C  S  T  P

1081   AGGGCAGATAGATTGTAACACGGGAAGCCGGGAAGTGAGAGAAAAGGGGATGAGTGCAGG   1320
 361    R  A  D  R  L  *

GCAGAGGTGAGGGAACCCAATAGTGATACCTGGTAAGGTGCTTCTTGCTCTTTTCCAGGC   1380
       TCTGGAGAGAAGCCCTCACCCTGAGGGTTGCCAGGGAGGCAGGGATATC             1429
```

FIG.1

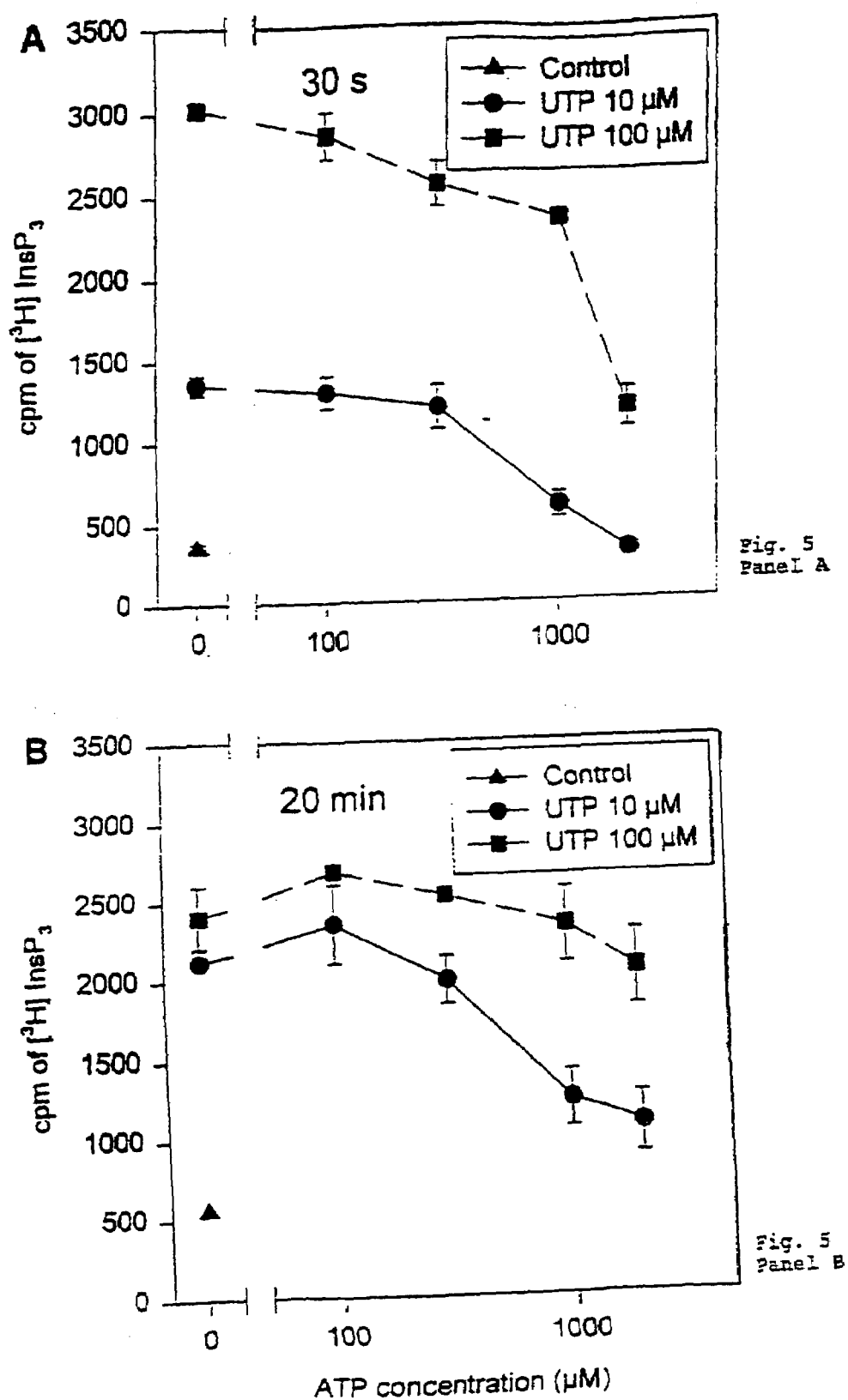
Fig. 5 Panel A
Fig. 5 Panel B

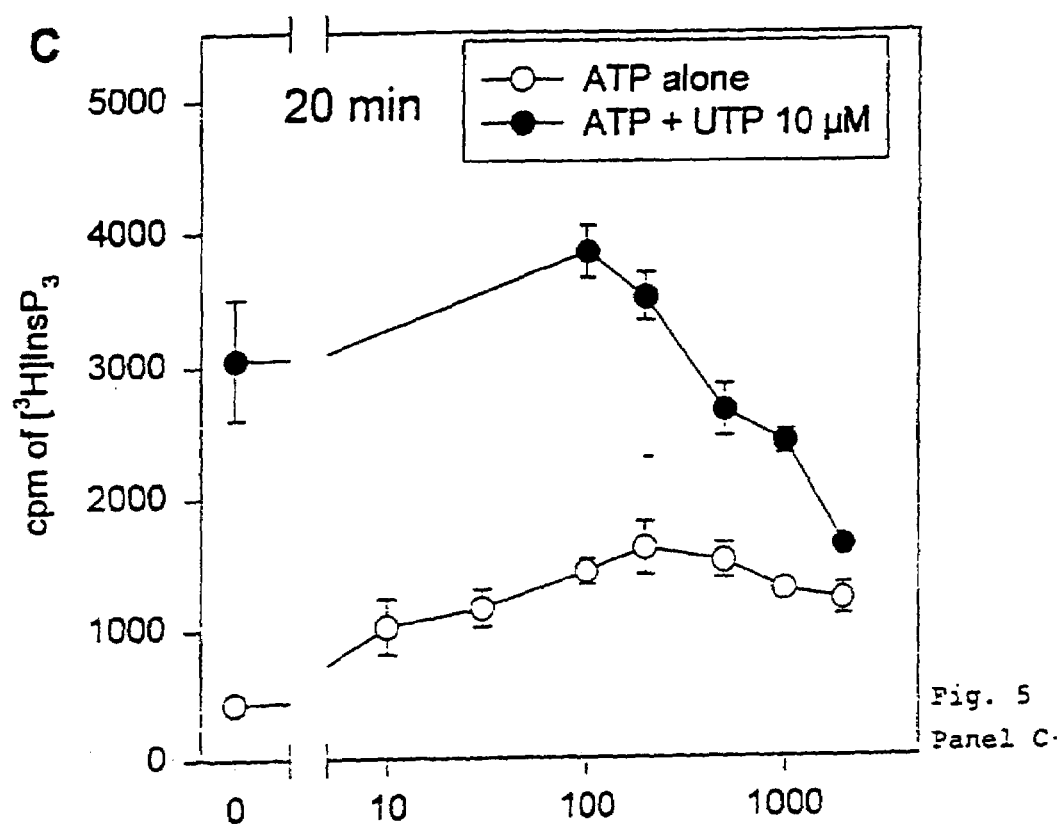
Fig. 5 Panel C

HUMAN PYRIMIDINE RECEPTOR

RELATED APPLICATIONS

This application is a divisional of application Ser. No. 09/077,173, filed Nov. 12, 1998 now U.S. Pat. No. 6,790,626 which is the U.S. National stage of International Application No. PCT/BE96/00123, filed on Nov. 21, 1996, which designated the United States and was published in English, which claims priority to foreign application EP 95870124.5 filed on Nov. 21, 1995. The entire teachings of the above application(s) are incorporated herein by reference.

OBJECT OF THE PRESENT INVENTION

The present invention concerns a new receptor having a preference for pyrimidine nucleotides preferably uridine triphosphate over purine nucleotides and the nucleic acid molecule encoding said receptor, vectors comprising said nucleic acid molecule, cells transformed by said vector, antibodies directed against said receptor, nucleic acid probes directed against said nucleic acid molecule, pharmaceutical compositions comprising said produces and non human transgenic animals expressing the receptor according to the invention or the nucleic acid molecule according to said receptor.

The invention further provides methods for determining ligand binding, detecting expression, screening for drugs, molecular binding specifically to said receptor and treatment involving the receptor according to the invention.

BACKGROUND

The cloning of several receptors for ATP has been reported since 1993. In keeping with the latest nomenclature proposal, these P2 purinergic receptors can be subdivided into two classes: G protein-coupled receptors, or P2Y receptors, and receptors with intrinsic ion channel activity or P2X receptors (2). Two distinct rat P2X receptors have been cloned, respectively from the vas deferens (3) and phaechromocytoma PC12 cells (4): they have a characteristic topology, with two hydrophobic putatively membrane-spanning segments and an ion pore motif reminiscent of potassium channels. In the P2Y family, the sequences of two subtypes, both coupled to phospholipase C, have been published: chick (5), turkey (6), bovine (7), mouse and rat (8) P2Y1 receptors (formerly called P2Y); murine (9, 10), rat (11) and human (12) P2Y2 receptors (previously named P2U) on the other hand. In addition, a P2Y3 receptor, with a preference for ADP over ATP, has been cloned from chick brain, but its sequence is not yet published (13). Furthermore, the 6H1 orphan receptor, cloned from activated chicken T lymphocytes, exhibits a significant degree of homology to the P2Y1 and P2Y2 receptors, suggesting that it also belongs to the P2Y family, although its responsiveness to nucleotides has not yet been demonstrated (14).

SUMMARY OF THE INVENTION

This invention provides a receptor having a preference for pyrimidine nucleotides preferably uridine triphosphate over purine nucleotides. A receptor having a preference for pyrimidine nucleotides over purine nucleotides means a receptor for which pyrimidine nucleotides and purine nucleotides are not equally active and equipotent. This means that the receptor according to the invention in presence of these agonists presents a functional response (preferably the accumulation of Inositol triphosphate (IP3), diacylglycerol (DAG), or calcium ions) to lower concentration of pyrimidine nucleotides, preferably uridine triphosphate, than to purine nucleotides or a more important functional response to similar concentration of pyrimidine nucleotide than to purine nucleotide.

The inositol phosphate (IP3) accumulation after addition of said agonists is described in the specification thereafter.

Advantageously, the receptor according to the invention has at least a twofold, preferably a tenfold to one hundredfold preference for pyrimidine nucleotides over purine nucleotides.

A preferred embodiment of the receptor according to the invention is characterized by a preference for uridine triphosphate over adenine nucleotides.

The receptor according to the invention is a receptor, preferably a G protein-coupled receptor, which belongs structurally to the purinergic receptor family (P2Y family) but functionally is a pyrimidinergic receptor, preferably a UTP-specific receptor.

According to a preferred embodiment of the present invention, the receptor is a human receptor.

Said receptor has an amino acid sequence having more than 60% homology with the amino acid sequence shown in FIG. 1. Preferably, the amino acid sequence of the receptor according to the invention has at least the amino acid sequence shown in FIG. 1 or a portion thereof.

A portion of the amino acid sequence means a peptide or a protein having the same binding properties as the receptor according to the invention (i.e. peptide or a protein which is characterized by a preference for pyrimidine nucleotides, preferably UTP, over purine nucleotides).

The present invention is also related to a nucleic acid molecule, such as a DNA molecule or an RNA molecule, encoding the receptor according to the invention.

Preferably, said DNA molecule is a cDNA molecule or a genomic DNA molecule.

Preferably, the nucleic acid molecule according to the invention is at least the DNA sequence shown in FIG. 1 or portion thereof. "A portion of a nucleic acid sequence" means a nucleic acid sequence encoding at least a portion of amino acid sequence as described above.

The present invention is also related to a vector comprising the nucleic acid molecule according to the invention. Preferably, said vector is adapted for expression in a cell and comprises the regulatory elements necessary for expressing the amino acid molecule in said cell operatively linked to the nucleic acid sequence according to the invention as to permit expression thereof.

Preferably, said cell is chosen among the group consisting of bacterial cells, yeast cells, insect cells or mammalian cells. The vector according to the invention is a plasmid or a virus, preferably a baculovirus, an adenovirus or a semliki forest virus.

The plasmid may be the pcDNA3-P2Y4.

The present invention concerns also the cell (preferably a mammalian cell, such as a 1321N1 cell) transformed by the vector according to the invention. Advantageously, said cell is preferably non neuronal in origin and is chosen among the group consisting of a COS-7 cell, an LM(tk-) cell, an NIH-3T3 cell or a 1321N1 cell.

The present invention is also related to a nucleic acid probe comprising the nucleic acid molecule according to the invention, of at least 15 nucleotides capable of specifically hybridizing with a unique sequence included in the sequence of the nucleic acid molecule encoding the receptor according to the invention. Said nucleic acid probe may be a DNA or an RNA molecule.

The invention concerns also an antisense oligonucleotide having a sequence capable of specifically hybridizing to an mRNA molecule encoding the receptor according to the invention so as to prevent translation of said mRNA molecule or an antisense oligonucleotide having a sequence capable of specifically hybridizing to the cDNA molecule encoding the receptor according to the invention.

Said antisense oligonucleotide may comprise chemical analogs of nucleotide or substances which inactivate mRNA, or be included in an RNA molecule endowed with ribozyne activity.

Another aspect of the present invention concerns a ligand other than purine and pyrimidine nucleotides (preferably an antibody) capable of binding to a receptor according to the invention and an anti-ligand (preferably also an antibody) capable of competitively inhibiting the binding of said ligand to the receptor according to the invention.

Preferably, said antibody is a monoclonal antibody.

The present invention concerns also the monoclonal antibody directed to an epitope of the receptor according to the invention and present on the surface of a cell expressing said receptor.

The invention concerns also the pharmaceutical composition comprising an effective amount of oligonucleotide according to the invention, effective to decrease the activity of said receptor by passing through a cell membrane and binding specifically with mRNA encoding the receptor according to the invention in the cell so as to prevent its translation. The pharmaceutical composition comprises also a pharmaceutically acceptable carrier capable of passing through said cell membrane.

Preferably, in said pharmaceutical composition, the oligonucleotide is coupled to a substance, such as a ribozyme, which inactivates mRNA.

Preferably, the pharmaceutically acceptable carrier comprises a structure which binds to a receptor on a cell capable of being taken up by cell after binding to the structure. The structure of the pharmaceutically acceptable carrier in said pharmaceutical composition is capable of binding to a receptor which is specific for a selected cell type.

Preferably, said pharmaceutical composition comprises an amount of the antibody according to the invention effective to block the binding of a ligand to the receptor according to the invention and a pharmaceutically acceptable carrier.

The present invention concerns also a transgenic non human mammal overexpressing (or expressing ectopically) the nucleic acid molecule encoding the receptor according to the invention.

The present invention also concerns a transgenic non human mammal comprising a homologous recombination knockout of the native receptor according to the invention.

According to a preferred embodiment of the invention, the transgenic non human mammal whose genome comprises antisense nucleic acid complementary to the nucleic acid according to the invention is so placed as to be transcribed into antisense mRNA which is complementary to the mRNA encoding the receptor according to the invention and which hybridizes to mRNA encoding said receptor, thereby reducing its translation. Preferably, the transgenic non human mammal according to the invention comprises a nucleic acid molecule encoding the receptor according to the invention and comprises additionally an inducible promoter or a tissue specific regulatory element.

Preferably, the transgenic non human mammal is a mouse.

The invention relates to a method for determining whether a ligand can be specifically bound to the receptor according to the invention, which comprises contacting a cell transfected with a vector expressing the nucleic acid molecule encoding said receptor with the ligand under conditions permitting binding of ligand to such receptor and detecting the presence of any such ligand bound specifically to said receptor, thereby determining whether the ligand binds specifically to said receptor.

The invention relates to a method for determining whether a ligand can specifically bind to a receptor according to the invention, which comprises preparing a cell extract from cells transfected with a vector expressing the nucleic acid molecule encoding said receptor, isolating a membrane fraction from the cell extract, contacting the ligand with the membrane fraction under conditions permitting binding of the ligand to such receptor and detecting the presence of any ligand bound to said receptor, thereby determining whether the compound is capable of specifically binding to said receptor. Preferably, said method is used when the ligand is not previously known.

The invention relates to a method for determining whether a ligand is an agonist of the receptor according to the invention, which comprises contacting a cell transfected with a vector expressing the nucleic acid molecule encoding said receptor with the ligand under conditions permitting the activation of a functional receptor response from the cell and detecting by means of a bio-assay, such as a modification in a second messenger concentration or a modification in the cellular metabolism (preferably determined by the acidification rate of the culture medium), an increase in the receptor activity, thereby determining whether the ligand is a receptor agonist.

The invention relates to a method for determining whether a ligand is an agonist of the receptor according to the invention, which comprises preparing a cell extract from cells transfected with a vector expressing the nucleic acid molecule encoding said receptor, isolating a membrane fraction from the cell extract, contacting the membrane fraction with the ligand under conditions permitting the activation of a functional receptor response and detecting by means of a bio-assay, such as a modification in the production of a second messenger an increase in the receptor activity, thereby determining whether the ligand is a receptor agonist.

The present invention relates to a method for determining whether a ligand is an antagonist of the receptor according to the invention, which comprises contacting a cell transfected with a vector expressing the nucleic acid molecule encoding said receptor with the ligand in the presence of a known receptor agonist, under conditions permitting the activation of a functional receptor response and detecting by means of a bio-assay, such as a modification in second messenger concentration or a modification in the cellular metabolism, (preferably determined by the acidification rate of the culture medium) a decrease in the receptor activity, thereby determining whether the ligand is a receptor antagonist.

The present invention relates to a method for determining whether a ligand is an antagonist of the receptor according to the invention, which comprises preparing a cell extract from cells transfected with an expressing the nucleic acid molecule encoding said receptor, isolating a membrane fraction from the cell extract, contacting the membrane fraction with the ligand in the presence of a known receptor agonist, under conditions permitting the activation of a functional receptor response and detecting by means of a bio-assay, such as a modification in the production of a second messenger, a decrease in the receptor activity, thereby determining whether the ligand is a receptor antagonist.

Preferably, the second messenger assay comprises measurement of intracellular cAMP, intracellular inositol phosphate (IP3), intracellular diacylglycerol (DAG) concentration or intracellular calcium mobilization.

Preferably, the cell used in said method is a mammalian cell non neuronal in origin, such as a COS-7 cell, a CHO cell, a LM(tk-) cell an NIH-3T3 cell or 1321N1.

In said method, the ligand is not previously known.

The invention is also related to the ligand isolated and detected by any of the preceding methods.

The present invention concerns also the pharmaceutical composition which comprises an effective amount of an agonist or an antagonist of the receptor according to the invention, effective to reduce the activity of said receptor and a pharmaceutically acceptable carrier.

For instance, said agonist or antagonist may be used in a pharmaceutical composition in the treatment of cystic fibrosis, and the method according to the invention may be advantageously used in the detection of improved drugs which are used in the thereby determining whether the ligand is a receptor antagonist.

The present invention relates to a method for determining whether a ligand is an antagonist of the receptor according to the invention, which comprises preparing a cell extract from cells transfected with an expressing the nucleic acid molecule encoding said receptor, isolating a membrane fraction from the cell extract, contacting the membrane fraction with the ligand in the presence of a known receptor agonist, under conditions permitting the activation of a functional receptor response and detecting by means of a bio-assay, such as a modification in the production of a second messenger, a decrease in the receptor activity, thereby determining whether the ligand is a receptor antagonist.

Preferably, the second messenger assay comprises measurement of intracellular cAMP, intracellular inositol phosphate (IP3), intracellular diacylglycerol (DAG) concentration or intracellular calcium mobilization.

Preferably, the cell used in said method is a mammalian cell non neuronal in origin, such as a COS-7 cell, a CHO cell, a LM(tk-) cell an NIH-3T3 cell or 1321N1.

In said method, the ligand is not previously known.

The invention is also related to the ligand isolated and detected by any of the preceding methods.

The present invention concerns also the pharmaceutical composition which comprises an effective amount of an agonist or an antagonist of the receptor according to the invention, effective to reduce the activity of said receptor and a pharmaceutically acceptable carrier.

For instance, said agonist or antagonist may be used in a pharmaceutical composition in the treatment of cystic fibrosis, and the method according to the invention may be advantageously used in the detection of improved drugs which are used in the treatment of cystic fibrosis.

Therefore, the previously described methods may be used for the screening of drugs to identify drugs which specifically bind to the receptor according to the invention.

The invention is also related to the drugs isolated and detected by any of these methods.

The present invention concerns also a pharmaceutical composition comprising said drugs and a pharmaceutically acceptable carrier.

The invention is also related to a method of detecting expression of a receptor according to the invention by detecting the presence of mRNA coding for a receptor, which comprises obtaining total RNA or total mRNA from the cell and contacting the RNA or mRNA so obtained with the nucleic acid probe according to the invention under hybridizing conditions and detecting the presence of mRNA hybridized to the probe, thereby detecting the expression of the receptor by the cell.

Said hybridization conditions are stringent conditions.

The present invention concerns also the use of the pharmaceutical composition according to the invention for the treatment and/or prevention of cystic fibrosis.

The present invention concerns also a method for diagnosing a predisposition to a disorder associated with the activity of the receptor according to the invention. Said method comprises:

a) obtaining nucleic acid molecules of subjects suffering from said disorder;

b) performing a restriction digest of said nucleic acid molecules with a panel of restriction enzymes;

c) electrophoretically separating the resulting nucleic acid fragments on a sized gel;

d) contacting the resulting gel with a nucleic acid probe capable of specifically hybridizing to said nucleic acid molecule and labeled with a detectable marker;

e) detecting labeled bands which have hybridized to the said nucleic acid molecule labeled with a detectable marker to create a unique band pattern specific to subjects suffering from said disorder;

f) preparing nucleic acid molecules obtained for diagnosis by step a-e; and g) comparing the unique band pattern specific to the nucleic acid molecule of subjects suffering from the disorder from step e and the nucleic acid molecule obtained for diagnosis from step f to determine whether the patterns are the same or different and to diagnose thereby predisposition to the disorder if the patterns are the same.

A last aspect of the present invention concerns a method of preparing the receptor according to the invention, which comprises:

a) constructing a vector adapted for expression in a cell which comprises the regulatory elements necessary for the expression of nucleic acid molecules in the cell operatively linked to nucleic acid molecule encoding said receptor so as to permit expression thereof, wherein the cell is selected from the group consisting of bacterial cells, yeast cells, insect cells and mammalian cells;

b) inserting the vector of step a in a suitable host cell;

c) incubating the cell of step b under conditions allowing the expression of the receptor according to the invention;

d) recovering the receptor so obtained; and e) purifying the receptor so recovered, thereby preparing an isolated receptor according to the invention.

BRIEF DESCRIPTION OF THE DRAWINGS

FIG. 1 represents the nucleotide and deduced amino acid sequence of a human $P2Y_4$ receptor according to the invention. SEQ ID NO:1 and SEQ ID NO:2, respectively. The putative membrane-spanning domains are underlined and numbered I to VII. The consensus sequence conserved between all the P2Y receptors and the three amino acids (AHN) corresponding to the RGD sequence in the first extracellular loop of the $P2Y_2$ receptor are represented in bold. The putative phosphorylation sites by PKC or by calmodulin-dependent protein kinases and PKC are indicated respectively by black squares (■) and by open circles (○).

FIG. 5 Represents the effect of ATP on the accumulation of $InsP_3$ induced by UTP in 1321N1 transfected cells. Concentration-action curves of ATP in the presence of UTP 10 or 100 μM at 30 s (panel A) and 20 min (panel B). Concentration-action curve of ATP with or without UTP (10 μM) at 20 min (panel C). The data represent the mean±S.D. of triplicate experimental points and are representative of two (panel A), five (panel B) or three (panel C) independent experiments.

The cells were incubated with UTP, UDP, 5BrUTP, dUTP, ITP, $AP_3A$, $AP_4A$, $AP_5A$ and $AP_6A$ at the same concentration of 100 μM or without agonist (Cont) for 30 s or 20 min. The data represent the mean±S.D. of triplicate experimental points and are representative of three independent experiments. The $EC_{50}$ values were determined by curve fitting (Sigma Plot: version 2.0).

Figure 8:
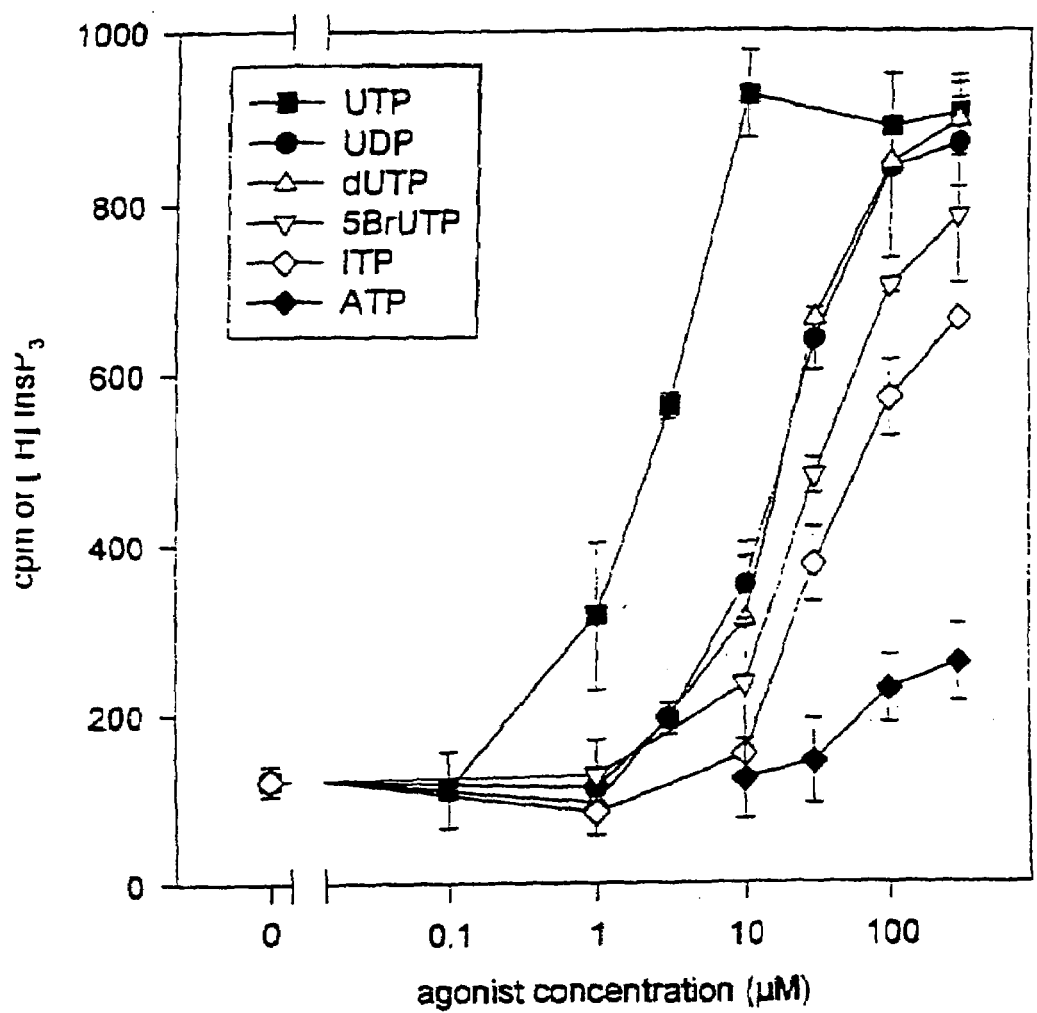

FIG. 8 Represents concentration-action curves of various nucleotides on the $InsP_3$ accumulation in 1321N1 cells expressing a human $P2Y_4$ receptor. 1321N1cells were incubated in the presence of various concentrations of UTP, UDP, dUTP, 5BrUTP, ITP and ATP for a period of time of 20 min. The data are the mean±range of duplicate experimental points obtained in an experiment representative of two.

Figure 9:
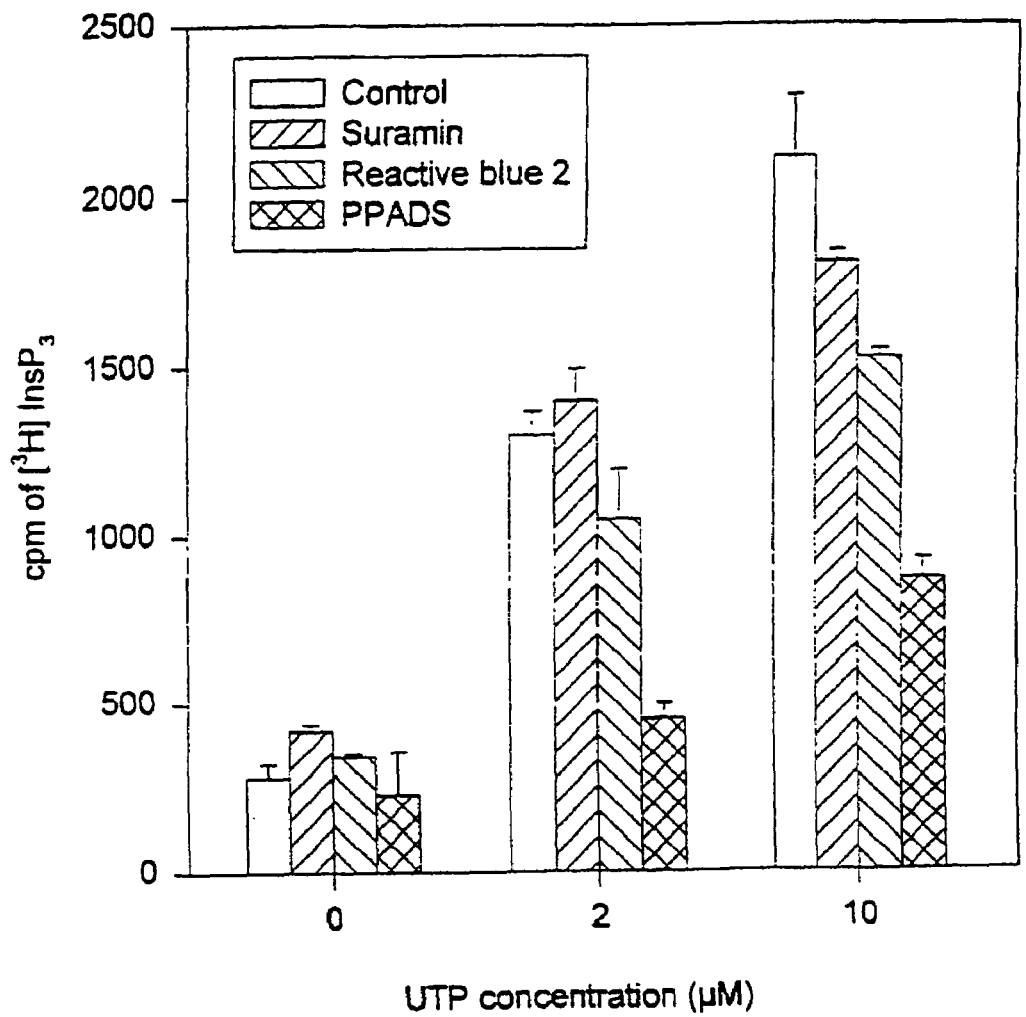

FIG. 9 Represents the action of various $P_2$ antagonists on the $InSP_3$ production induced by UTP in 1321N1 transfected cells. Cells were incubated in the presence of suramin, reactive blue 2 and PPADS at a concentration of 100 μM and different UTP concentrations (0, 2 and 10 μM) for 20 min. The data represent the mean±S.D. of triplicate experimental points and are representative of two independent experiments.

Figure 10:
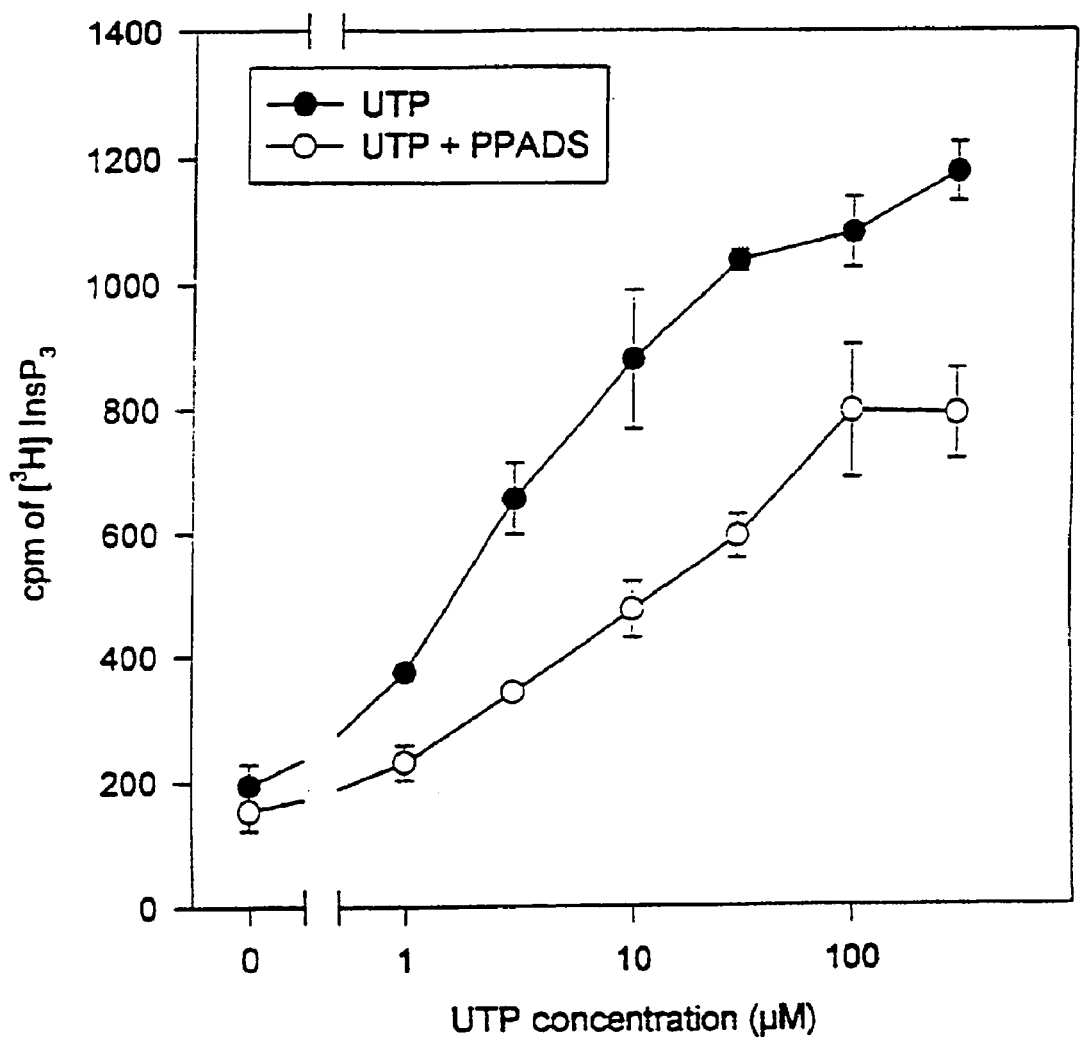

FIG. 10 Represents the effect of PPADS on the UTP stimulation of $InsP_3$ in 1321N1transfected cells. The cells were exposed to various concentrations of UTP in the presence or in the absence of PPADS (100 μM) for 20 min. The data are the mean±S.D. of triplicate experimental points obtained in an experiment representative of two.

Figure 11:
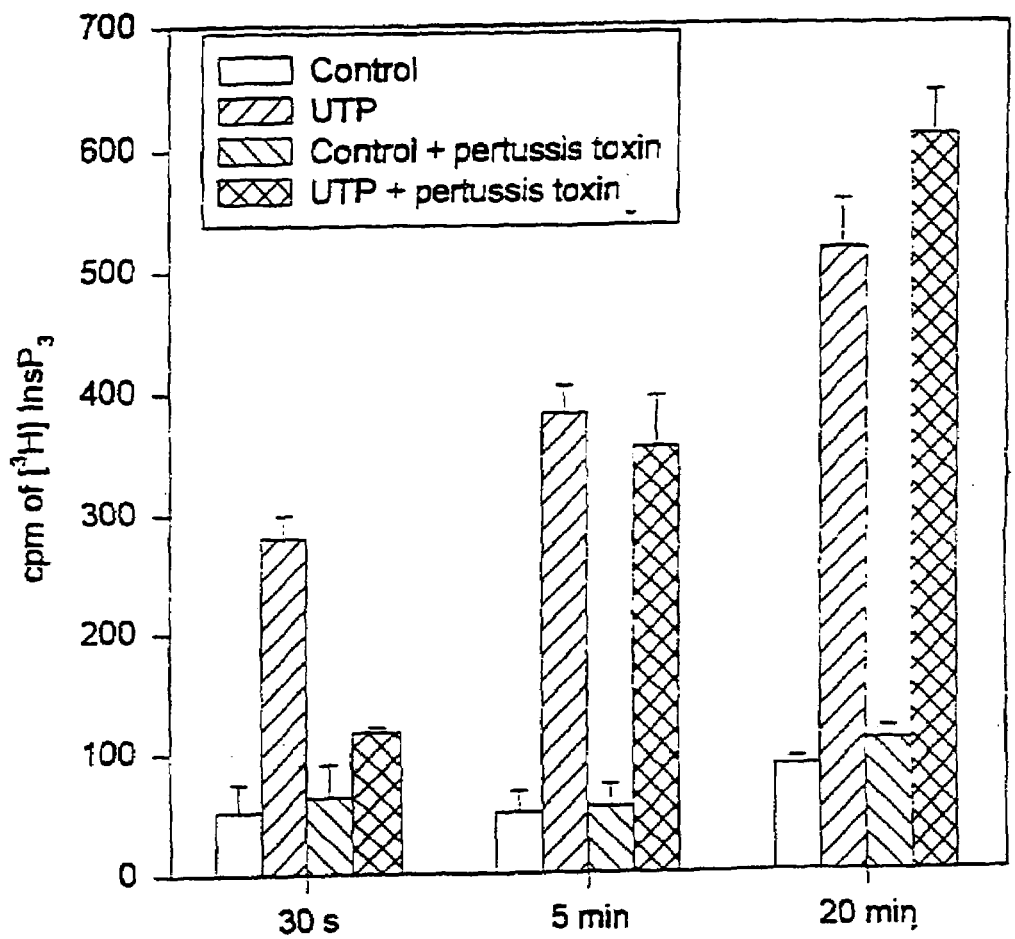

FIG. 11 Represents the effect of pertussis toxin on the UTP-induced accumulation of $InSP_3$ in 1321N1cells expressing a human $P2Y_4$ receptor. The cells were preincubated for 18 hours in the presence or in the absence of 20 ng/ml pertussis toxin. The cells were then incubated with or without UTP 100 μM and with or without pertussis toxin (20 ng/ml) for various times: 30 s, 5 min or 20 min. The data represent the mean±S.D. of triplicate experimental points and are representative of two independent experiments.

DETAILED DESCRIPTION OF THE INVENTION

Experimental Procedures

1. Materials

Trypsin was from Flow Laboratories (Bioggio, Switzerland) and the culture media, reagents, G418, fetal calf serum (FCS), restriction enzymes and Taq polymerase were purchased from GIBCO BRL (Grand Island, N.Y.). The radioactive products myo-D-[2-$^3H$]inositol (17.7 Ci/mmol) and [$a^{32}P$]ATP (800 Ci/mmol) were from Amersham (Gent, Belgium). Dowex AG1X8 (formate form) was from Bio-Rad Laboratories (Richmond, Calif.). UTP, UDP, ATP, ADP, carbachol, LiCl and apyrase grade VII were obtained from Sigma Chemical Co. (St. Louis, Mo.). 2MeSATP was from Research Biochemicals Inc. (Natick, Mass.). pcDNA3 is an expression vector developed by Invitrogen (San Diego, Calif.).

2. Cloning and Sequencing

Degenerate oligonucleotide primers were synthesized on the basis of the best conserved segments between the murine P2Y2 and the chick P2Y1 receptor sequences. These primers were used to amplify novel receptor gene fragments by low-stringency PCR starting from human genomic DNA. The amplification conditions were as follows: 93° C. 1 min, 50° C. 2 min, 72° C. 3 min; 35 cycles. The PCR products with sizes compatible with P2 receptor gene fragrnents were subcloned in M13mp18 and M13mp19 and sequenced by the Sanger dideoxy nucleotide chain termination method. One of the resulting clones sharing similarities with P2 receptors, was labeled by random priming and used to screen a human genomic DNA library constructed in the λ Charon 4a vector. The hybridization was in 6×SSC (1×SSC: 0.15 M NaCl, 0.015 M Sodium citrate) and 40% formamide at 42° C. for 14 h and the final wash conditions were 0.1×SSC, 0.1% SDS at 65° C. A preparation of λ phages (15) was made for several clones which hybridized strongly with the probe. A restriction map and a Southern blotting analysis allowed to isolate a 1.4 kb NheI-EcoRV fragment that was subcloned into the pBluescript SK⁻ vector (Stratagene). The complete sequence of a new receptor coding sequence was obtained on both strands after subdloning of overlapping fragments in M13mp18 and M13mp19.

3. Cell Culture and Transfection

The $P2Y_4$ receptor coding sequence was subdloned between the HindIII and the EcoRV sites of the pcDNA3 expression vector for transfection into 1321N1 human astrocytoma cells, a cell line which does not respond to nucleotides and which has already been used for the expression of purinergic receptors (6, 12). Cells were transfected with the recombinant pcDNA3 plasmid (pcDNA3-P2Y$_4$) using the calcium phosphate precipitation method as described (16). 1321N1 cells were incubated for 6 hours at 37° C. in the presence of pcDNA3 vector alone or vector containing the P2Y$_4$ receptor coding sequence, then washed and incubated in culture medium (10% FCS, 100 U/ml penicillin, 100 µ/ml streptomycin and 2.5 µg/ml amphotericin B in Dulbecco's modified Eagle's medium (DMEM)). The selection with G418 (400 µg/ml) was started two days after transfection. From the pool of transfected 1321N1 cells, individual clones were isolated by limiting dilution with the aim of selecting clones with high IP stimulation factors in response to nucleotides. The different clones were maintained in a medium containing 400 µg/ml G418.

4. Inositol Phosphates (IP) Measurement

1321N1 cells were labeled for 24 hours with 10 µCi/ml [$^3$H] inositol in inositol-free DMEM (Dulbecco's modified Eagle's medium) medium containing 5% fetal calf serum, 100 U/ml penicillin, 100 µg/ml streptomycin, 2.5 µg/ml amphotericin B and 400 µg/ml G418. Cells were washed twice with KRH (Krebs-Ringer Hepes) buffer of the following composition: (124 mM NaCl, 5 mM KCl, 1.25 mM MgSC$_4$, 1.45 mM CaCl$_2$, 25 mM Hepes (pH 7.4) and 8 mM glucose) and incubated in this medium for 30 min The agonists were added in the presence of LiCl (10 mM) and the incubation was stopped after 30 s, 5 min or 20 min by the addition of an ice-cold 3% perchloric acid solution. For the time course study, LiCl (10 mM) was added 5 min before the agonists and the incubation was stopped at different times. When tested, pertussis toxin (20 ng/ml) was added for 18 h during the labeling period time and during the stimulation by the agonist. Inositol phosphates were extracted and InsP$_3$ was isolated by chromatography on Dowex column as described previously (17).

5. Radioligand Binding Assay.

Binding assays of [$\alpha^{32}$P] UTP to cell membranes were carried out in Tris-HCl (50 mM, pH 7.5), EDTA 1 mM in a final volume of 0.5 ml, containing 25-50 µg of protein and 0.5 nM of radioligand (27). The assays were conducted at 30° C. for 5 min. Incubations were stopped by the addition of 4 ml of ice-cold Tris-HCl (50 mM, pH 7.5) and rapid filtration through Whatman GF/B filters under reduced pressure. The filters were then washed three times with 2 ml of the same ice-cold Tris-HCl buffer. Radioactivity was quantified by liquid scintillation counting, after an overnight incubation of the filters in liquid scintillation mixture.

6. Northern Blot and Southern Blot Analysis

Total and poly(A)$^+$RNA were prepared from different tissues and human cell lines using the guanidinium thiocyanate-cesium chloride procedure (15), denatured by glyoxal and fractionated by electrophoresis on a 1% agarose gel in 10 mM phosphate buffer pH 7.0. DNA samples, prepared from the λ Charon 4a clones, were digested with restriction enzymes. Northern and Southern blots were prepared (15) and baked for 90 min at 80° C. Membranes were prehybridized for at least 4 hours and hybridized overnight with the same probe as for the screening, at 42° C. in a solution containing 50% formamide for Northern blots and 40% formamide for Southern blots. Filters were washed twice for 15 min in 2×SSC at room temperature and then twice for 30 min in 0.2×SSC at 60° C. before being exposed at −70° C. in the presence of intensifying screens for 5 days (Northern blots) or 1 hour (Southern blots).

Results

1. Cloning and Sequencing

In order to isolate new subtypes of P2 receptors, sets of degenerate oligonucleotide primers were synthesized on the basis of the best conserved segments in the published sequences of the chick brain P2Y1 (5) and murine neuroblastoma P2Y2 (9) receptors. These primers were used in low-stringency PCR on human genomic DNA as described (18). Some combinations generated discrete bands with a size compatible with that expected for P2 receptors. For example, the primer [5'-CAGATCTAGATA(CT)ATGTT(CT)(AC)A(CT)(CT)T(ACGT) GC-3'] (SEQ ID NO:3) corresponding to the second transmembrane region and the primer [5'-TCTTAAGCTTGG(AG)TC(ACG-T)A(CG)(AG)CA(AG)CT(AG) TT-3'] (SEQ ID NO:4) corresponding to the seventh transmembrane region amplified a 712 bp fragment. The partial sequences obtained after sequencing were translated into peptidic sequences and compared to a local databank which contains G protein-coupled receptor sequences. Most of the clones resulting from these PCR products encoded a part of a new receptor which displayed 58% identity with the murine P2Y2 receptor and 42% identity with the chick P2Y1 receptor partial sequences. In addition, some clones encoded a peptidic sequence presenting 87% identity with the chick P2Y1 receptor and are therefore believed to represent fragments of the human P2Y1 gene.

Figure 2:
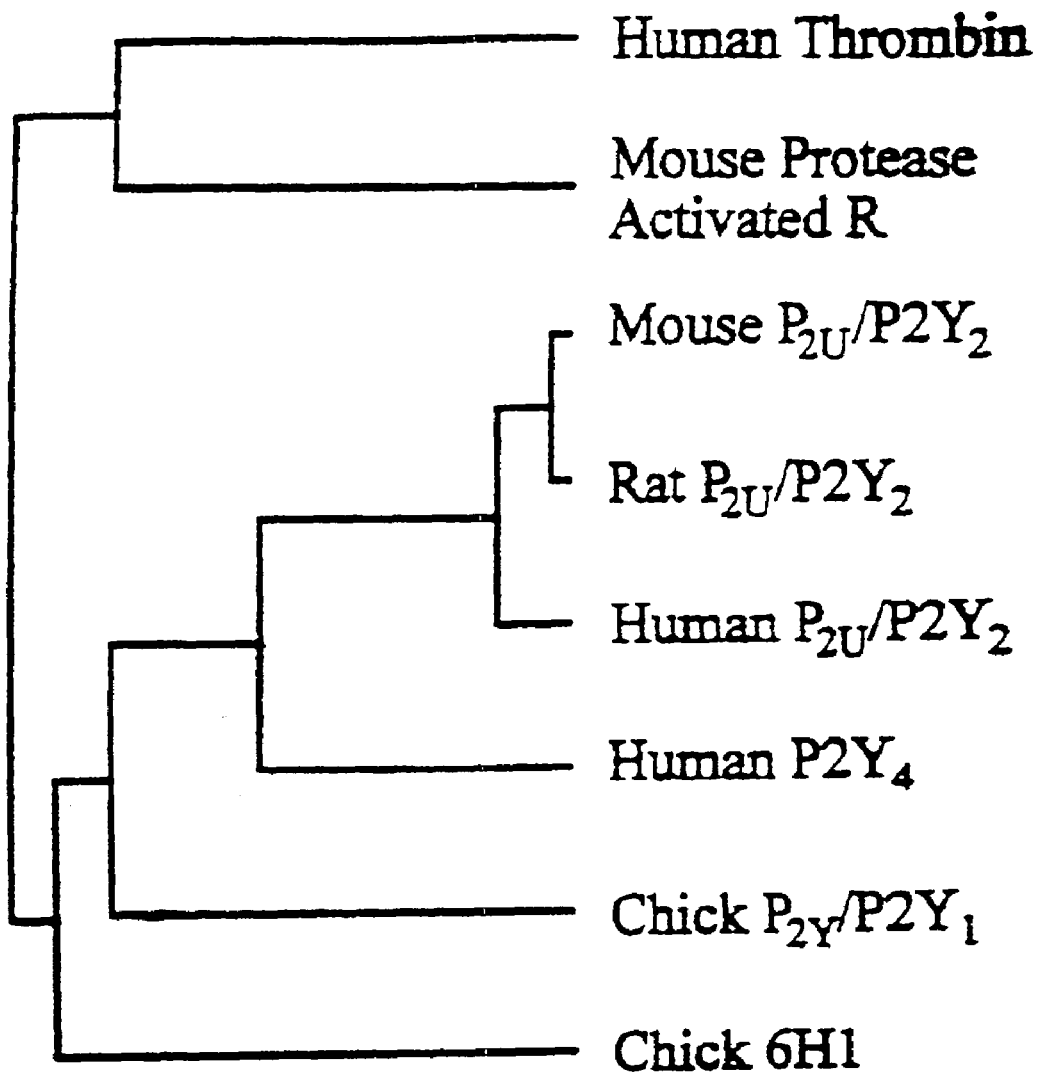
FIG. 2 is a dendrogram representing structural relatedness among the cloned P2Y receptor and the closest neighbour in the G protein-coupled receptor family. The plot was constructed using the multiple sequence alignment program Pileup of the GCG package (26). For each sequence, the analysis takes into account a segment covering the first five putative membrane-spanning domains.

The partial sequence of the new receptor was used as a probe to screen a human genomic DNA library. Several clones that strongly hybridized with the probe at high stringency conditions were obtained and purified. The inserts of the clones varied from 12 to 17 kb and restriction analysis revealed that all clones belonged to a single locus. The full sequence of a 1.4 kb NheI-EcoRV fragment was obtained and an intronless open reading frame of 1095 bp was identified. The sequence is depicted in FIG. 1 where the putative membrane-spanning domains are underlined and numbered I to VII. The predicted molecular weight of the encoded protein is 36.5 kDa. This molecular weight is unlikely to be modified in vivo, since no N-glycosylation consensus sequences are found in the putative exofacial regions. In contrast with the human P2Y2 receptor, there is no RGD motif, an integrin binding consensus sequence, in the putative first extracellular loop. The three amino acid (AHN) corresponding to the RGD sequence in the first extracellular loop of the P2Y2 receptor are represented in bold in FIG. 1. Some potential sites of phosphorylation by protein kinase C (PKC) or by calmodulin-dependent protein kinases were identified in the third intracellular loop and in the carboxyterminal part of the receptor. The putative phosphorylation sites by PKC or by calmodulin-dependent protein kinases and PKC are indicated respectively by black squares and by open circles in FIG. 1. The four positively charged amino acid which have been reported to play a role in the P2Y2 receptor activation by ATP and UTP (1) are conserved in the P2Y4 sequence: His$^{262}$, Arg$^{265}$, Lys$^{289}$ and Arg$^{292}$ (FIG. 1). The P2Y4 amino acid sequence was compared to the chick P2Y1 and the murine P2Y2 amino acid sequences and to their closest neighbours in the G protein-coupled receptor family (FIG. 2). The plot was constructed using the multiple sequence alignment program Pileup of the GCG package (26). For each sequence, the analysis takes into account a segment covering the first five putative membrane-spanning domains. It is clear that, from a structural point of view, the newly cloned receptor is more closely related to the human P2Y2 receptor (51% of identity between the complete sequences) than to the chick P2Y1 receptor (35%).

2. Tissue Distribution of the P2Y4 Receptor

Figure 3:
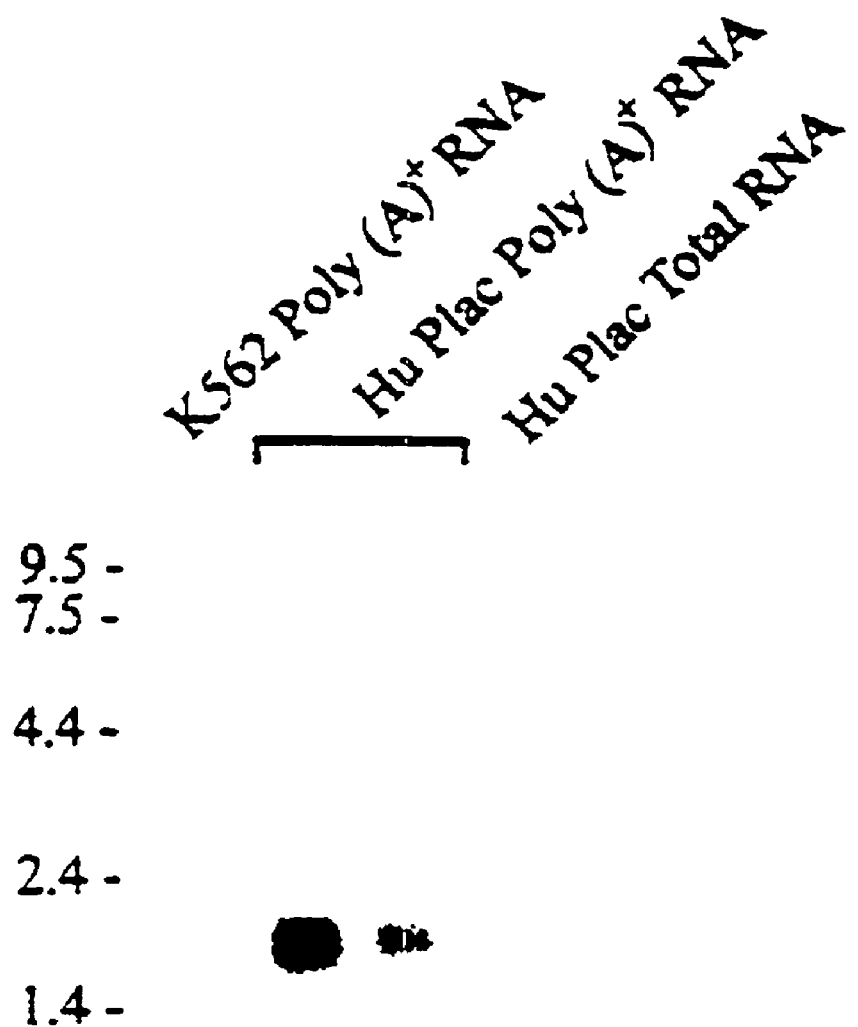
FIG. 3 represents a northern blot analysis of $P2Y_4$ receptor expression. The Northern blot was performed with 15 μg of total RNA from human placenta and 4 μg of poly(A)$^+$ RNA from K562 cells and from two different human placentas. The probe was a human $P2Y_4$ gene fragment amplified by PCR (TM2 to TM7).

The tissue distribution of P2Y4 transcripts was investigated by Northern blotting. A number of rat tissues (heart, brain, liver, testis and kidney) were tested using a human probe at low stringency, but no hybridization signal could be obtained. No P2Y4 transcript could be detected in the following human cell lines: K562 leukemia cells (FIG. 3), HL-60 leukemia cells and SH-SY5Y human neuroblastoma cells. The Northern blot was performed with 15 μg of total RNA from human placenta and 4 μg of poly(A)$^+$RNA from K562 cells and from two different human placentas. The probe was the human P2Y4 gene fragment amplified by PCR (TM2 to TM7). On the contrary, a strong signal, corresponding to a 1.8 kb mRNA, was found in human placenta (FIG. 3).

3. Functional Expression of the New P2 Receptor in 1321N1 Cells

Figure 4:
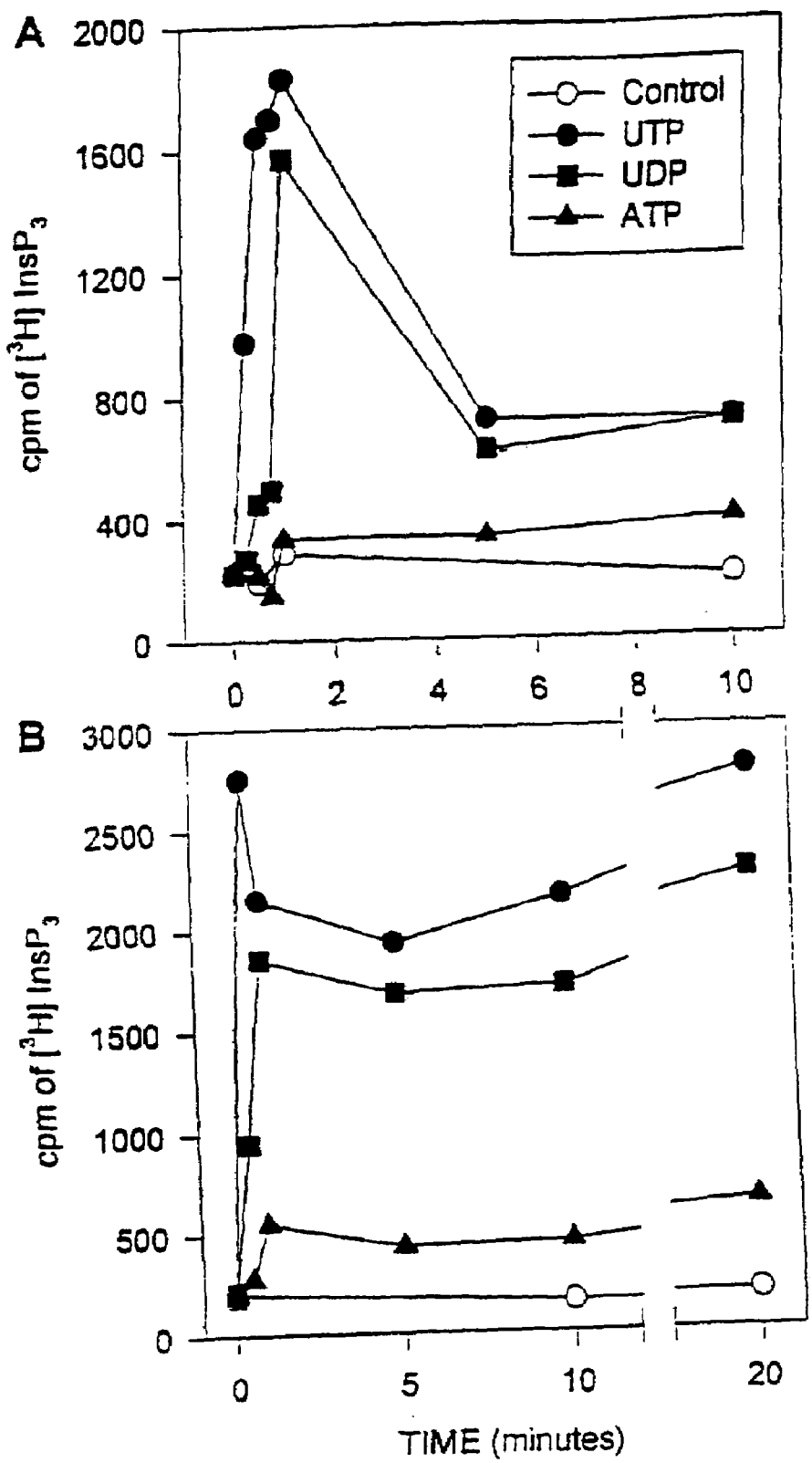
FIG. 4 represents the time course of $InsP_3$ accumulation in 1321N1 cells expressing the human $P2Y_4$ receptor. $^3H$ inositol labelled cells were incubated for the indicated time with UTP (100 μM), UDP (100 μM) and ATP (100 μM) in the absence of 10 mM LiCl (panel A) or in its presence (panel B). The data represent the mean of triplicate experimental points and are representative of two independent experiments.

After transfection of the pcDNA3-P2Y4 construction in 1321N1 cells, the pool of G418-resistant clones was tested for their functional response (IP3 accumulation) to ATP and UTP. Both nucleotides were found to be agonists of the P2Y4 receptor, but the response to UTP was more robust. About 20 transfected clones were then isolated and tested for their response to UTP. The clone presenting the highest IP accumulation factor in response to UTP was selected and used in all subsequent experiments. Functional characterization of the $P2Y_4$ receptor was performed by determining the accumulation of $InSP_3$ after 20 min incubation with the agonists in the presence of 10 mM LiCl. We observed that the response to UTP was biphasic, with a peak reached at 30 s, followed by a more sustained stimulation of lower magnitude (FIG. 4A). With ATP, only that second phase was detectable: its effect became apparent after 1 min of stimulation only and was stable for at least 20 min (FIGS. 4A and B). As for UTP, the stimulation by UDP was biphasic, but it was slightly delayed (FIGS. 4A and B). Inclusion of LiCl had little effect on the initial peak induced by UTP or UDP, but it strongly enhanced the following plateau phase (FIG. 4B).

The maximal effect of ATP observed after a 20 min incubation represented about 27±9% of that of UTP (mean±S.D. of ten experiments). In order to demonstrate that ATP is able to antagonize the UTP response, incubations of 1321N1 cells were conducted with ATP alone or in combination with UTP. FIG. 5 shows that at high concentration (500 μM or more), ATP was able to inhibit the effect of UTP, both at 30 s and 20 min At 30 s, the response to UTP 10 μM was fully antagonized by ATP 2 mM, corresponding to the fact that ATP has no effect on the human $P2Y_4$ receptor at this early time (panel A). At 20 min, an inhibition of 62±11% of the UTP effect (10 μM), corresponding to the difference between the UTP and the ATP effects, was observed in the presence of 2 mM ATP (mean±S.D. of five independent experiments) (panels B and C). The ATP concentration-inhibition curves were shifted to the right when the UTP concentration was increased, indicating the competitive nature of this inhibitory effect (panels A and B). On the other hand, at lower concentrations (30-300 μM), ATP enhanced the response to UTP by 29% (range 12-47%, mean of four experiments) (panel B). ADP, which had almost no effect per se and did not inhibit the action of UTP, reproduced that enhancement: in the presence of ADP (100 μM), the stimulation by UTP (10 μM) represented 158±15% (mean of three independent experiments) of that by UTP alone (data not shown). However, this potentiating effect of ATP and ADP was not specific: indeed the action of carbachol mediated by muscarinic receptors endogenously expressed in the 1321N1 cells (6) was also increased in the presence of these nucleotides. This observation was reproduced with cells transfected with the recombinant $P2Y_4$-pcDNA3 plasmid or with the vector alone and was also obtained with AMP and adenosine (data not shown).

Figure 6:
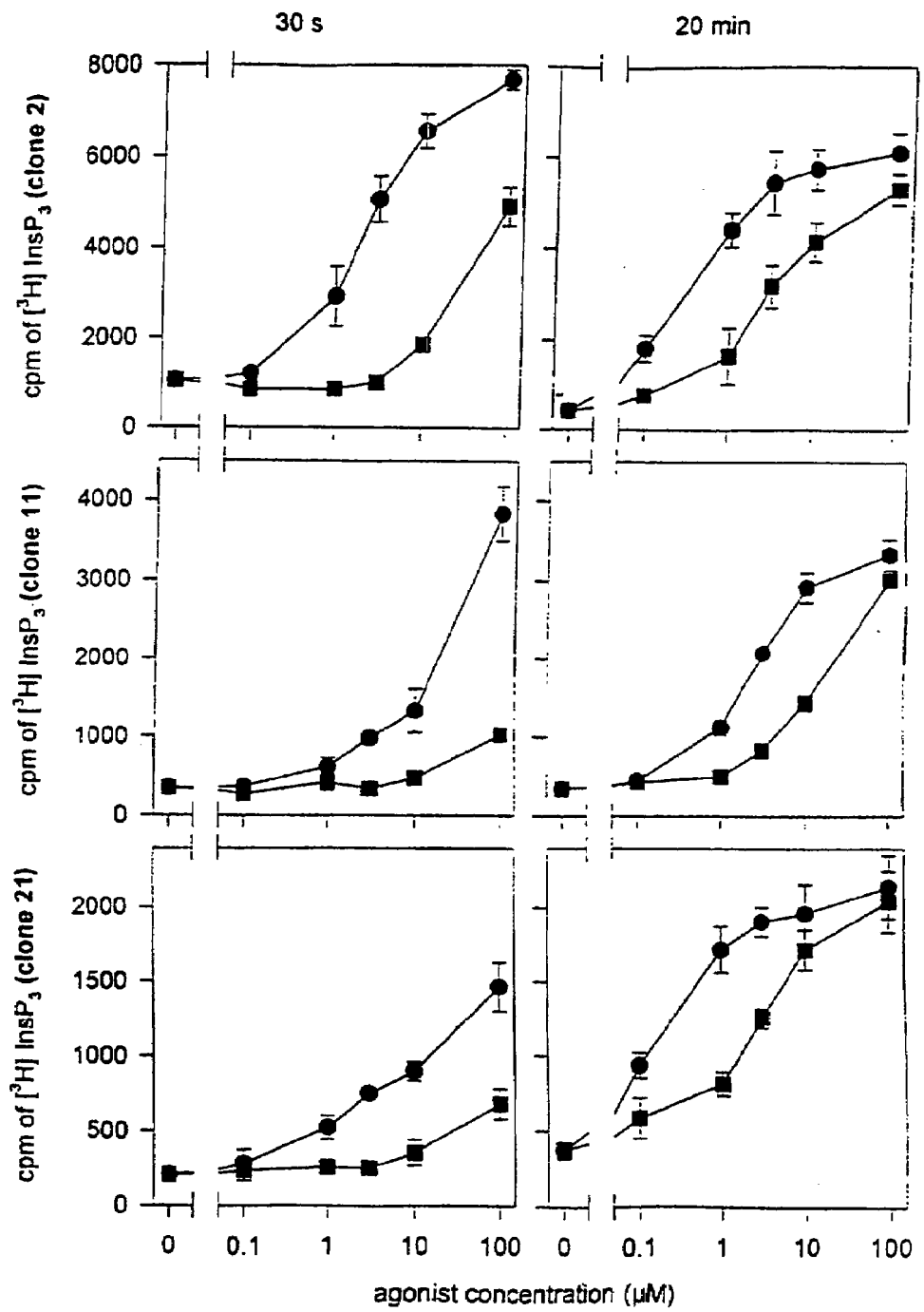
FIG. 6 represents the concentration-action curves of UTP and UDP on the $InSP_3$ accumulation in three different clones of 1321N1 transfected cells. The cells were incubated in the presence of various UTP (●) and UDP (■) concentrations (0, 0.1, 1, 3, 10 and 100 μM) for 30 s or 20 min. The data represent the mean±S.D. of triplicate experimental points obtained in one representative experiment. The $EC_{50}$ values were determined by curve fitting (Sigma Plot: version 2.0).

We compared the concentration-action curves of UTP and UDP on the $InSP_3$ production for several clones of transfected cells. The study was made at two times (FIG. 6): 30 s and 20 min. In the set of experiments performed on clone 11 (clone of 1321N1 transfected cells chosen for the pharmacological characterization), UTP appeared to be 10-fold more potent than UDP after a 20 min incubation and this difference was reproduced with two other clones (FIG. 6). The $EC_{50}$ values were 0.3±0.1 μM and 3.3±0.6 μM in clone 2, 2.4±0.1 μM and 19.8±4.8 μM in clone 11 and 0.3±0.1 μM and 3.2±0.8 μM in clone 21, respectively, for UTP and UDP (mean±S.D. of two independent experiments). At 30 s of incubation, it was not possible to determine $EC_{50}$ values because the curves were clearly shifted to the right, but we can observe that the difference between the two agonists potency was even more striking (FIG. 6). Several clones, including clones 2, 11 and 21 were tested in binding studies with $[\alpha^{32}P]$ UTP but no increase in specific binding was observed as compared to the cells transfected with the vector alone (data not shown).

Figure 7:
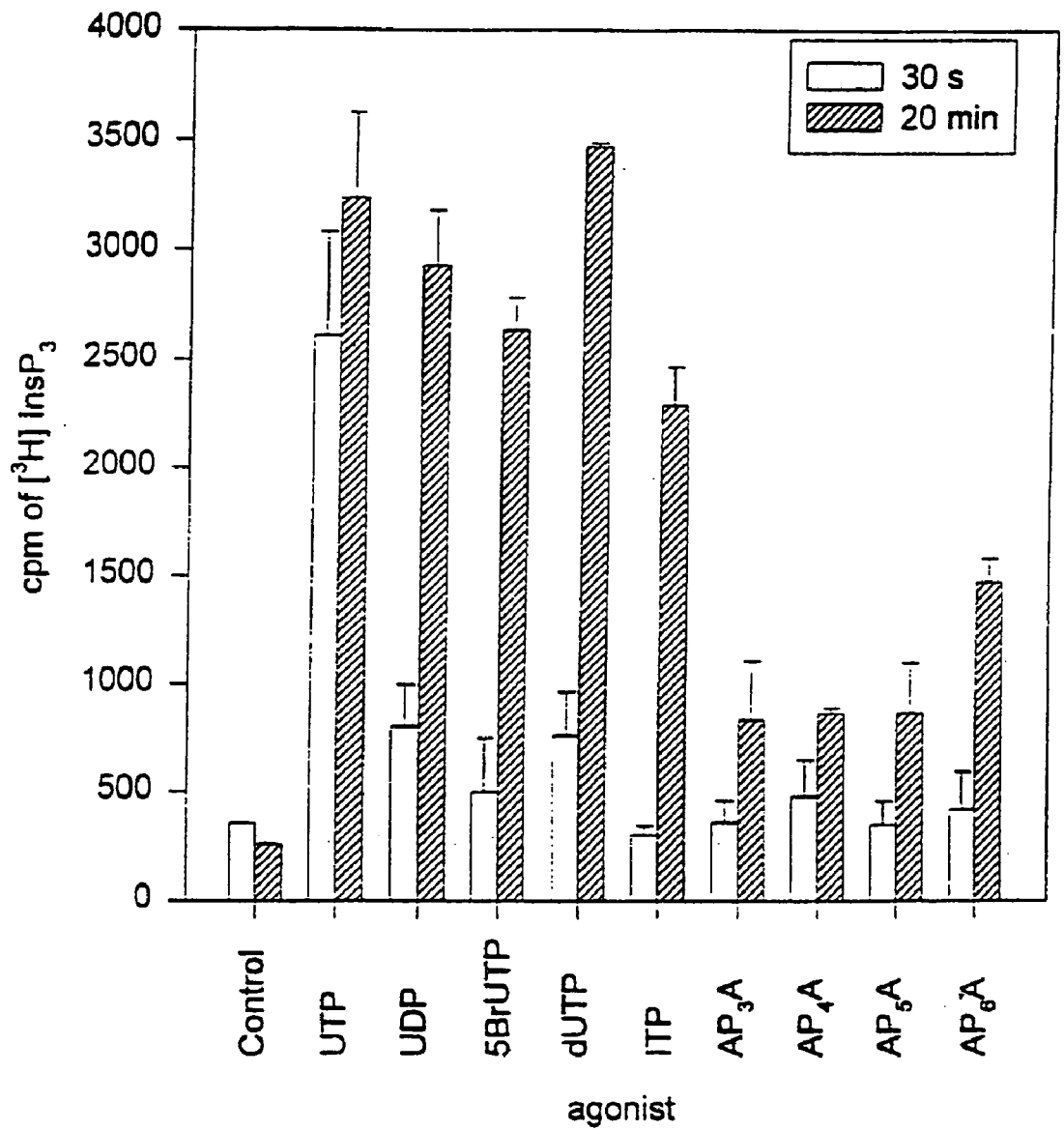
FIG. 7 Represents the effect of various nucleotides on the $InSP_3$ production in 1321N1 transfected cells.

In view of the time differences observed in FIG. 6, the testing of a range of nucleotides was performed at two times: 30 s and 20 min. As FIG. 7 shows, several agonists were barely or not active at 30 s (UDP, 5BrUTP, dUTP, ITP) whereas they produced a significant effect at 20 min. Full concentration-action curves were obtained at 20 min. The rank order of potency was: UTP>UDP=dUTP>5BrUTP>ITP>ATP (FIG. 8). The $EC_{50}$ values obtained were the following: $EC_{50}$UTP=2.5±0.6 μM, $EC_{50}$ UDP=19.5±3.9 μM (mean±S.D. of eight independent experiments), $EC_{50}$ dUTP=20.0±2.3 μM, $EC_{50}$ 5BrUTP=27.1±1.9 μM and $EC_{50}$ ITP=32.8±5.4 μM (mean±S.D. of two independent experiments). The approximative $EC_{50}$ value obtained for ATP was: 43±12 μM (mean±S.D. of five independent experiments). The diadenosine polyphosphates also increased the $InSP_3$ production in transfected cells with $EC_{50}$ between 3 and 7 μM (data not shown), but their maximal effect was only 20-25% of that of UTP, a value close to that of ATP (range of four independent experiments) (FIG. 7). UMP, uridine, AMP, adenosine and ATPyS were without any effect (data not shown).

No specific antagonist is available for any P2Y subtype. Nonetheless, several non-selective antagonists such as suramin, RB2 or PPADS have been tested on $P_2$ receptors and their relative actions on these subtypes may constitute a mean to discriminate them (27). So we tested the ability of these three antagonists to inhibit the UTP response in the model of the human $P2Y_4$ receptor. As we can see on FIG. 9, PPADS appeared to be the most active antagonist (73±14% inhibition; $IC_{50}$ around 15 μM (data not shown)), suramin was inactive, and RB-2 produced an inhibition of 33±5% of the UTP response (mean±S.D. of two independent experiments). FIG. 10 shows the mixed nature of the antagonism by PPADS of the UTP response: it affects both the $EC_{50}$ value and the maximal effect of UTP. The $EC_{50}$ value for UTP in the absence of PPADS was 3.3±0.6 μM and 12.2±4.5 μM in the presence of 100 μM PPADS (mean±S.D. of two independent experiments).

The effect of pertussis toxin (20 ng/ml, 18 hours pretreatment) was studied at different times after UTP (100 μM) addition (FIG. 11). The UTP response was clearly inhibited at 30 s (62±5% of inhibition: mean±S.D. of two independent experiments), whereas no significant effect was observed at 5 and 20 min.

REFERENCES

1. Erb, L., Garrad, R., Wang, Y., Quinn, T., Turner, J. T., and Weisman, G. A. (1995) J. Biol. Chem. 270,4185-4188.
2. Fredholm, B. B., Abbracchio, M. P., Burnstock, G., Daly, J. W., Harden, T. K., Jacobson, K. A., Leff, P., and Williams, M. (1994) Pharm. Rev. 46, 143-156.
3. Valera, S., Hussy, N., Evans, R. J., Adami, N., North, R. A., Surprenant, A., and Buell, G. (1994) Nature 371, 516-519.
4. Brake, A. J., Wagenbach, M. J., and Julius, D. (1994) Nature 371, 519-523.
5. Webb, T. E., Simon, J., Krishek, B. J., Bateson, A. N., Smart, T. G., King, B. F., Burnstock, G., and Barnard, E. A. (1993) FEBS 324, 219-225.
6. Filtz, T. N., Li, Q., Boyer, J. L., Nicholas, R. A., and Harden, T. K. (1994) Mol. Pharm. 46, 8-14.
7. Henderson, D. J., Elliot, D. G., Smith, G. M., Webb, T. E., and Dainty, I. A. (1995) Biochem. Biophys. Res. Commun. 212, 648-656.
8. Tokoyama, Y., Hara, M., Jones, E. M. C., Fan, Z., and Bell, G. I. (1995) Biochem. Biophys. Res. Commun. 211, 211-218.
9. Lustig, K. D., Shiau, A. K., Brake, A. J., and Julius, D. (1993) Proc. Natl. Acad. Sci. 90, 5113-5117.
10. Erb, L., Lustig, K. D., Sullivan, D. M., Turner, J. T., and Weisman, G. A. (1993) Proc Natl Acad Sci 90, 10449-10453.
11. Rice, W. R., Burton, F. M., and Fiedeldey, D. T. (1995) Am. J. Respir. Cell, Molec. Biol. 12, 27-32.
12. Parr, C. E., Sullivan, D. M., Paradiso, A. M., Lazarowski, E. R., Burch, L. H., Olsen, J. C., Erb, L., Weisman, G. A., Boucher, R. C., and Turner, J. T. (1994) Proc. Natl. Acad. Sci. 91, 3275-3279.
13. Barnard, E. A., Burnstock, G., and Webb, T. E. (1994) TiPS 15, 67-70.
14. Kaplan, M. H., Smith, D. I., and Sundick, R. S. (1993) J. Immun. 151, 628-636.
15. Sambrook, J., Fritsch, E. F., and Maniatis, T. (1989) Molecular Cloning: A laboratory Manual (Cold Spring Harbor Lab. Press, Plainview, N.Y.).
16. Velu, T. J., Beguinot, L., Vass, W. C., Zhang, K., Pastan, I., and Lowry, D. R. (1989) J. Cell. Biochem. 39, 153-166.
17. Communi, D., Raspe, E., Pirotton, S., and Boeynaems, J. M. (1995) Circ. Res. 76, 191-198.
18. Libert, F., Parmentier, M., Lefort, A., Dinsart, C., Van Sande, J., Maenhaut, C., Simons, M. J., Dumont, J. E., and Vassart, G. (1989) Science 244, 569-572.
19. Zeng, D., Harrison, J. K., D'Angelo, D. D., Barber, C. M., Tucker, A. L., Lu, Z., and Lynch, K. R. (1990) Proc. Natl. Acad. Sci. 87, 3102-3106.
20. Nomura, H., Nielsen, B. W., and Matsushima, K. (1993) Int. Immun. 5, 1239-1249.
21. Harrison, J. K., Barber, C. M., and Lynch, K. R. (1994) Neuroscience Letters 169, 85-89.
22. Seifert, R. and Schultz, G. (1989) TiPS 10, 365-369.
23. Brown, H. A., Lazarowski, E. R., Boucher, R. C., and Harden, T. K. (1991) Mol. Pharm. 40, 648-655.
24. O'Connor, S. E., Dainty, I. A., and Leff, P. (1991) TiPS 12, 137-141.
25. Lazarowski, E. R. and Harden, T. K. (1994) J. Biol. Chem. 269, 11830-11836.
26. Devereux, J., Haeberli, P. and Smithies O. A. (1984) Nucleic Acids Res. 12, 387-395.
27. Motte S., Swillens S. and Boeynaems J. M. (1996) Eur. J. Pharmacol. 307, 201.
28. Boyer, J. L., Zohn, I. E., Jacobson, K. A. and Harden, T. K. (1994) Br. J. Pharmacol. 113, 614.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method for determining whether a ligand can specifically bind to a receptor, wherein said receptor comprises the amino acid sequence shown in SEQ ID NO:2, comprising the following steps:

i) preparing a cell extract from cells transfected with an expression vector comprising the nucleic acid molecule encoding said receptor, ii) isolating a membrane fraction from the cell extract, iii) contacting the ligand with the membrane fraction under conditions permitting binding of the ligand to said receptor, and iv) detecting the presence or absence of the ligand bound specifically to said receptor, wherein the presence of the ligand indicates that the ligand can specifically bind to said receptor.

2. The method of claim 1, wherein said receptor consists of the amino acid sequence shown in SEQ ID NO:2.

* * * * *

SEQUENCE LISTING

```
<160> NUMBER OF SEQ ID NOS: 4

<210> SEQ ID NO 1
<211> LENGTH: 1429
<212> TYPE: DNA
<213> ORGANISM: Homo sapiens

<400> SEQUENCE: 1
aagggagctt gggtaggggc caggctagcc tgagtgcacc cagatgcgct tctgtcagct      60
ctccctagtg cttcaaccac tgctctccct gctctacttt ttttgctcca gctcagggat     120
gggggtgggc agggaaatcc tgccaccctc acttctcccc ttcccatctc caggggggcc     180
atggccagta cagagtcctc cctgttgaga tccctaggcc tcagcccagg tcctggcagc     240
agtgaggtgg agctggactg ttggtttgat gaggatttca agttcatcct gctgcctgtg     300
agctatgcag ttgtctttgt gctgggcttg ggccttaacg ccccaaccct atggctcttc     360
```

-continued

```
atcttccgcc tccgaccctg ggatgcaacg gccacctaca tgttccacct ggcattgtca      420
gacaccttgt atgtgctgtc gctgcccacc ctcatctact attatgcagc ccacaaccac      480
tggccctttg gcactgagat ctgcaagttc gtccgctttc ttttctattg gaacctctac      540
tgcagtgtcc ttttcctcac ctgcatcagc gtgcaccgct acctgggcat ctgccaccca      600
cttcgggcac tacgctgggg ccgccctcgc ctcgcaggcc ttctctgcct ggcagtttgg      660
ttggtcgtag ccggctgcct cgtgcccaac ctgttctttg tcacaaccag caacaaaggg      720
accaccgtcc tgtgccatga caccactcgg cctgaagagt ttgaccacta tgtgcacttc      780
agctcggcgg tcatggggct gctctttggc gtgccctgcc tggtcactct tgtttgctat      840
ggactcatgg ctcgtcgcct gtatcagccc ttgccaggct ctgcacagtc gtcttctcgc      900
ctccgctctc tccgcaccat agctgtggtg ctgactgtct ttgctgtctg cttcgtgcct      960
ttccacatca cccgcaccat ttactacctg gccaggctgt ggaagctga ctgccgagta     1020 ctgaacattg tcaacgtggt ctataaagtg actcggcccc tggccagtgc caacagctgc     1080
ctggatcctg tgctctactt gctcactggg gacaaatatc gacgtcagct ccgtcagctc     1140
tgtggtggtg gcaagcccca gccccgcacg gctgcctctt ccctggcact agtgtccctg     1200
cctgaggata gcagctgcag gtgggcggcc acccccagg acagtagctg ctctactcct     1260
agggcagata gattgtaaca cgggaagccg gcaagtgaga gaaaagggga tgagtgcagg     1320
gcagaggtga gggaacccaa tagtgatacc tggtaaggtg cttcttcctc ttttccaggc     1380
tctggagaga agccctcacc ctgagggttg ccacggaggc agggatatc                 1429
```

<210> SEQ ID NO 2
<211> LENGTH: 365
<212> TYPE: PRT
<213> ORGANISM: Homo sapiens

<400> SEQUENCE: 2

```
Met Ala Ser Thr Glu Ser Ser Leu Leu Arg Ser Leu Gly Leu Ser Pro
1               5                   10                  15

Gly Pro Gly Ser Ser Glu Val Glu Leu Asp Cys Trp Phe Asp Glu Asp
            20                  25                  30

Phe Lys Phe Ile Leu Leu Pro Val Ser Tyr Ala Val Phe Val Leu
        35                  40                  45

Gly Leu Gly Leu Asn Ala Pro Thr Leu Trp Leu Phe Ile Phe Arg Leu
    50                  55                  60

Arg Pro Trp Asp Ala Thr Ala Thr Tyr Met Phe His Leu Ala Leu Ser
65                  70                  75                  80

Asp Thr Leu Tyr Val Leu Ser Leu Pro Thr Leu Ile Tyr Tyr Ala
                85                  90                  95

Ala His Asn His Trp Pro Phe Gly Thr Glu Ile Cys Lys Phe Val Arg
            100                 105                 110

Phe Leu Phe Tyr Trp Asn Leu Tyr Cys Ser Val Leu Phe Leu Thr Cys
        115                 120                 125

Ile Ser Val His Arg Tyr Leu Gly Ile Cys His Pro Leu Arg Ala Leu
    130                 135                 140

Arg Trp Gly Arg Pro Arg Leu Ala Gly Leu Leu Cys Leu Ala Val Trp
145                 150                 155                 160

Leu Val Val Ala Gly Cys Leu Val Pro Asn Leu Phe Phe Val Thr Thr
                165                 170                 175

Ser Asn Lys Gly Thr Thr Val Leu Cys His Asp Thr Thr Arg Pro Glu
            180                 185                 190
```

```
Glu Phe Asp His Tyr Val His Phe Ser Ser Ala Val Met Gly Leu Leu
        195                 200                 205

Phe Gly Val Pro Cys Leu Val Thr Leu Val Cys Tyr Gly Leu Met Ala
        210                 215                 220

Arg Arg Leu Tyr Gln Pro Leu Pro Gly Ser Ala Gln Ser Ser Ser Arg
225                 230                 235                 240

Leu Arg Ser Leu Arg Thr Ile Ala Val Val Leu Thr Val Phe Ala Val
                245                 250                 255

Cys Phe Val Pro Phe His Ile Thr Arg Thr Ile Tyr Tyr Leu Ala Arg
                260                 265                 270

Leu Leu Glu Ala Asp Cys Arg Val Leu Asn Ile Val Asn Val Val Tyr
        275                 280                 285

Lys Val Thr Arg Pro Leu Ala Ser Ala Asn Ser Cys Leu Asp Pro Val
        290                 295                 300

Leu Tyr Leu Leu Thr Gly Asp Lys Tyr Arg Arg Gln Leu Arg Gln Leu
305                 310                 315                 320

Cys Gly Gly Lys Pro Gln Pro Arg Thr Ala Ala Ser Ser Leu Ala
                325                 330                 335

Leu Val Ser Leu Pro Glu Asp Ser Ser Cys Arg Trp Ala Ala Thr Pro
                340                 345                 350

Gln Asp Ser Ser Cys Ser Thr Pro Arg Ala Asp Arg Leu
        355                 360                 365

<210> SEQ ID NO 3
<211> LENGTH: 35
<212> TYPE: DNA
<213> ORGANISM: artificial sequence
<220> FEATURE:
<223> OTHER INFORMATION: Primer for the second transmembrane region of
      human pyrimidine receptor

<400> SEQUENCE: 3
cagatctaga tactatgttc tacactctta cgtgc                           35

<210> SEQ ID NO 4
<211> LENGTH: 35
<212> TYPE: DNA
<213> ORGANISM: artificial sequence
<220> FEATURE:
<223> OTHER INFORMATION: primer for seventh transmembrane region of
      human pyrimidine receptor

<400> SEQUENCE: 4
tcttaagctt ggagtcacgt acgagcaagc tagtt                           35
```